United States Patent

Merianos et al.

Patent Number: 5,209,922
Date of Patent: May 11, 1993

[54] WATER SOLUBLE POLYMERS HAVING ANTIFUNGAL PROPERTIES

[75] Inventors: John J. Merianos, Middletown; Herbert A. Lieberman, Livingston; Paul Garelick, South Plainfield, all of N.J.

[73] Assignee: ISP Investments Inc., Wilmington, Del.

[21] Appl. No.: 855,358

[22] Filed: Mar. 19, 1992

[51] Int. Cl.$^5$ .................. A61K 9/12; A61K 31/785
[52] U.S. Cl. .......................... 424/46; 424/47; 424/78.14; 424/78.72; 424/78.25; 424/409; 424/DIG. 5
[58] Field of Search ............ 514/260; 424/70, 78.04, 424/78.24, 78.36, 46, 47, 78.14, 78.22, 78.25, 469, DIG. 5

[56] References Cited

U.S. PATENT DOCUMENTS

| | | | |
|---|---|---|---|
| 2,776,924 | 1/1957 | Martin | 424/78.02 |
| 4,329,336 | 5/1982 | Su et al. | 424/70 |
| 4,513,008 | 4/1985 | Revici et al. | 514/560 |
| 4,520,132 | 5/1985 | Kinsolving | 514/560 |
| 4,704,436 | 11/1987 | Barabas | 424/78.2 X |
| 4,978,525 | 12/1990 | Ohyama et al. | 424/70 |

FOREIGN PATENT DOCUMENTS 0311281  4/1989  European Pat. Off. .......... 424/78.24

Primary Examiner—Thurman K. Page
Assistant Examiner—Peter Kulkosky
Attorney, Agent, or Firm—Marilyn J. Maue; Joshua J. Ward

[57] ABSTRACT

This invention relates to an antifungal block copolymer of poly(vinyl lactam) having the formula

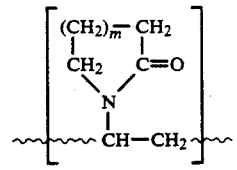

where m has a value of from 1 to 3 and from about 15 to about 25 wt. % of a quaternized amino alkyl acrylamide comonomer wherein the quaternizing anion is in part halide $-O-CO(CH_2)_sCH=CHZ$ wherein s has a value of from 4 to 14 and Z is hydrogen or a $C_1$ to $C_4$ alkyl radical, which copolymer is comprised of the following units

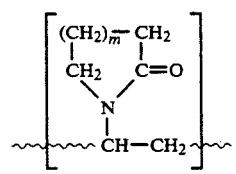

A.

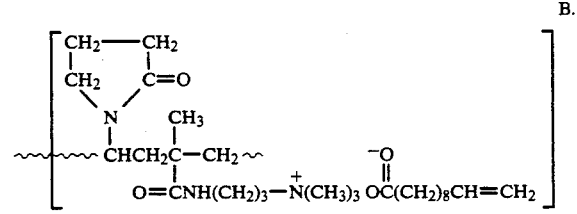

B.

and

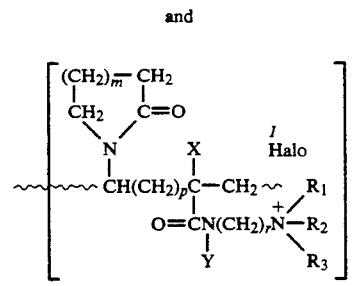

C.

wherein m has a value of from 1 to 3; p has a value of from 1 to 5; r has a value of from 2 to 6; each of X and Y is hydrogen or a $C_1$ to $C_4$ alkyl and each of $R_1$, $R_2$ and $R_3$ is $C_1$ to $C_4$ alkyl. The invention also relates to the use of the above polymers as antifungal agents.

17 Claims, No Drawings

WATER SOLUBLE POLYMERS HAVING ANTIFUNGAL PROPERTIES

In one aspect, the invention relates to novel acid quaternized amino amido alkenyl lactam polymers, which are suitably employed for antifungal medicinal uses. In another aspect, the invention relates to the use of said polymers as suitable for plant and skin applications.

BACKGROUND OF THE INVENTION

The antifungal properties of undecylenic acid salts are well known; however, a major drawback in the wide spread use of this and similar acid salts is attributable to their limited solubility in water. Accordingly, compositions containing commercially available undecylenic sodium, calcium or zinc salts require complex and costly carrier systems to provide undecylenic acid powder or liquid in a composition which readily absorbs moisture so as to maximize its antifungal properties.

Accordingly, it is an object of this invention to provide a fungicidal undecylenic acid compound in a form which is water and perspiration soluble and which is economically prepared in a wide variety of formulations containing carriers or solvents that are not usually compatible with undecylenic acid per se.

Another object of this invention is to offer a water soluble undecylenic compound which provides fungicidal protection for an extended time period by a gradual release of its fungicidal active ingredient.

Another object is to provide a process for the use of compounds containing undecylenic moieties as water soluble antifungal agents.

These and other objects of the invention will become apparent from the following description and disclosure.

THE INVENTION

In accordance with this invention there is provided an antifungal, water soluble block copolymer consisting essentially of between 75% and 85% poly(vinyl lactam) units defined as

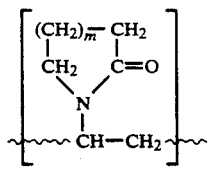

A.

and between about 15 wt. % and about 25 wt. of the quaternized amino alkyl acryl amide lactam units defined as

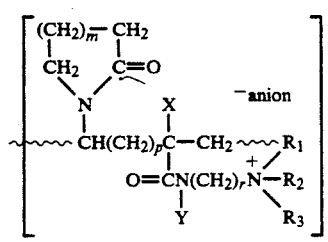

BC.

wherein said anion is between about 10% and 90% by weight halide and the remaining 10% to 90% is —O—CO(CH$_2$)$_s$CH=CHZ; and wherein
- m has a value of from 1 to 3;
- p has a value of from 1 to 5;
- r has a value of from 2 to 6;
- s has a value of from 4 to 14;
- each of X, Y and Z is hydrogen or a $C_1$ to $C_4$ alkyl and each of $R_1$, $R_2$ and $R_3$ is $C_1$ to $C_4$ alkyl.

The molecular weight of the present polymers ranges between about 180,000 and about 2,000,000; preferably between about 190,000 and about 1,700,000 and the polymers contain from about 500 to about 2,000, preferably from about 800 to about 1,500, of the unit BC.

Preferred among this group of polymers are those wherein m has a value of 1;
- s s has a value of from 6 to 9; and
- $R_1$, $R_2$ and $R_3$ are each individually methyl or ethyl.

Most preferred are the polymers containing 10% to 18% of the units

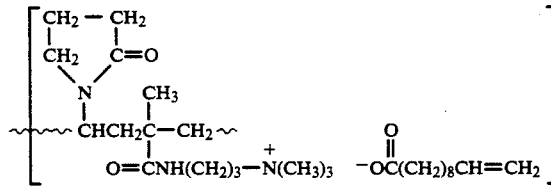

Undecylenic acid is known to have antifungal properties; however its use is restricted by its limited water solubility. Accordingly, the amount of quaternized units and the proportions of halide and alkenylate anions in the present polymer is critical to the present invention. More specifically, the alkenylate provides the antifungal activity, while the halide is needed to solubilize the active alkenylate moieties, to extend the antifungal activity and to provide the film forming properties of the polymer. Although the above quaternized polymers are readily employed as aqueous solutions containing up to 90% or more water, aqueous $C_1$ to $C_3$ alcohol, propylene glycol, cyclohexane, tetrahydrofuran, etc., the present polymers are most desirably used in powder form and are particularly useful in the topical treatment of athletes foot and other fungal skin ailments. As aqueous solutions, they are also useful as plant sprays to control fungal infestation. In addition, they may be added to any standard fungicidal liquid or powder formulation for increased affect and extended fungicidal activity.

The polymers of this invention are readily prepared by reacting a $C_7$ to $C_{17}$ mono-unsaturated acid salt of ammonia, an alkali or alkaline earth metal with a halogen quaternized amino amido alkenyl lactam/poly(N-vinyl lactam) block copolymer, such as GAFQUAT® HS-100, which is poly(N-vinylpyrrolidone/methacrylamidopropyl trimethyl ammonium chloride copolymer, or GAFQUAT® 734, which is poly(N-vinylpyrrolidone/dimethylaminoethylmethacrylate methyl chloride salt. Both are supplied by International Specialty Products. The reaction is carried out at a temperature between about 50° and about 80° C. under from about 50 to 200 mm Hg pressure with a synthesis time of from 2 to 8 hours. The preferred synthesis reaction conditions include a temperature of from about 60° to about 80° C. under from about 100 to 150 mm Hg pressure for between about 3.5 and about 6 hours. In the above reaction, the ratio of the unsaturated acid salt to the quaternized lactam polymer is as close to stoichiomatry as is convenient to maintain. However, a slight excess of the halo quaternized lactam polymer reactant, up to about 25% excess, can be employed without detriment. The reaction is carried out in the liquid phase in the presence of a suitable inert monomer solvent such as a $C_1$ to $C_3$ alcohol, water, propylene glycol, etc. and mixtures thereof. The concentration of the solvent in the reaction mixture can vary from about 10 to about 50 weight but is more often present in an amount between about 15 and about 25 weight %. The product of the reaction is readily recovered by solvent evaporation, followed by drying at a suitable temperature. The reaction, which takes place at the quaternized sites of the copolymer, is represented by the equation

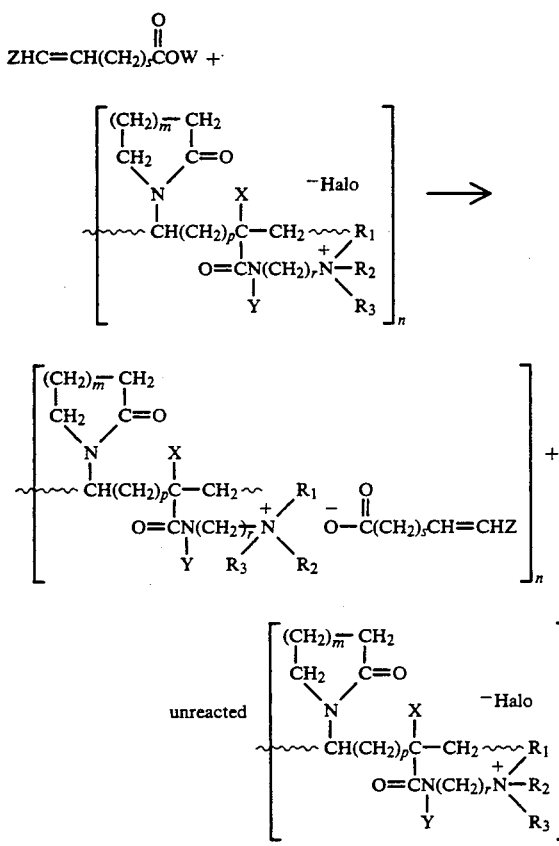

wherein W is ammonium, an alkali metal or an alkaline earth metal and halo is chlorine, bromine or iodine and other lettered subscripts and substituents are as defined above.

The polymers of this invention are useful as antifungal agents which are employed as powders or as aqueous solutions. For example, compositions containing from about 15 to about 85 weight % polymer are effective.

Suitable carriers for the present antifungal polymers when used in a dry condition include zinc oxide, talc, starch, silica, kaolin, calcium phosphate and the like. Formulations of instant quaternized polymers can additionally include a deodorant, antiperspirant, fragrance and/or coloring agent. The compositions of the present invention can also contain a lubricant, e.g. in an amount of from about 1 up to about 8 wt. % for creams and powders but may contain up to about 30 wt. % when used in a dry deodorant stick. Other ingredients which may be present in the composition include a neutralizer in an amount between about 0.5 and about 5 wt. %, a humectant in an amount of from 2 to 10 wt. %, a moisturizer in an amount of from about 0.1 to about 5 wt. %; an astringent in an amount between about 1 and about 3 wt. %; a dehydrating agent in an amount between about 0.1 and about 3 wt. % and, for a solid dry stick or bar, a hardening agent in an amount of from about 15 to about 30 wt. %. Alternatively, the present quaternized polymers can be added to a commercial antifungal formulation for increased efficacy.

In addition to their solubility properties, the present compounds are capable of providing controlled release of the active unsaturated ester anion which possesses the active antifungal property. It is to be understood that mixtures as well as individual esteric anions of this invention can be employed to provide the fungicidal moieties in the polymer. Other uses for the present polymers involve their disinfecting properties for use in treating cuts and skin infections. Aqueous solutions of the present polymers can also be applied safely to plants in the above concentrations to control bacteria and fungi infestation. Many other uses will become apparent from the above description and disclosure.

Having generally described the invention, reference is now made to the following examples which illustrate specific and preferred examples but which are not to be construed as limiting the scope of the invention as more broadly set forth above and in the appended claims.

EXAMPLE 1

I Preparation of the Quaternized Polymer Complex

To sodium undecylenate (20.6 g) dissolved 100 ml methanol, was added 120 g. of poly(vinylpyrrolidione/-methacrylamidopropyl trimentyl ammonium chloride (GAFQUAT® HS-100) dissolved in 500 ml of methanol. The solutions were heated to about 55° C. and mixed for 2 hours to provide a hazy suspension of fine particles. The resulting mixture was then cooled to 0° C., and sodium chloride (4.2 g) was filtered off as a white precipitate. The filtrate was then evaporated to remove methanol and dried under vacuum to give 135.6 g of the quaternized polymer containing 5% units of

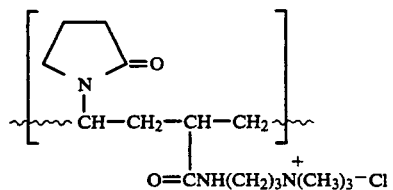

and 8% units of

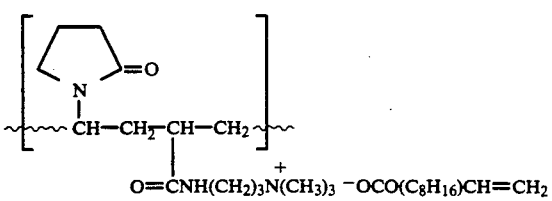

II The above quaternized GAFQUAT® complex, designated as HS-100/UA, is employed in the following foot antifungal formulations.

| POWDER | | |
|---|---|---|
| A. | Ingredients | Wt. % |
| | Talc | 77.7 |
| | Oil Fragrance | 0.8 |
| | GLUCAM® P-20* | 1.5 |
| | HS-100/UA | 20.0 |
| | Preservative (optional) | QS |

The above composition is prepared by premixing a dry master batch of oil, GLUCAM® P-20, HS-100/UA and 5% of the talc. This dry mixture is then added to the remaining portion of talc and mixed at room temperature until a uniform composition is obtained.

The above formulation is useful as a foot powder or after shave powder, which may be converted to flesh tone by the addition of an iron oxide pigment.

| DUST | | |
|---|---|---|
| B. | Ingredients | Wt. % |
| | Talc | 80.0 |
| | Magnesium carbonate | 1.6 |
| | Zinc Stearate | 2.0 |
| | Oil Fragrance | 0.2 |
| | GLUCAM® P-20* | 1.3 |
| | HS-100/UA | 15.0 |
| | Preservative | QS |

*the methyl glucose ether of polypropylene glycol, supplied by Amerchol Corp.

This formulation is prepared by premixing a dry master batch of HS-100/UA, oil, GLUCAM® P-20 and 5% of the talc and then adding the remaining talc and other ingredients while mixing at room temperature until a uniform composition is obtained.

For greater coverage, zinc oxide or titanium dioxide can be added to the formulation.

In addition to a foot powder, the above composition can be used as a deodorant after bath dusting powder.

| MOISTURIZING CREAM | | |
|---|---|---|
| C. | Ingredients | Wt. % |
| I | VEEGUM® PRO [1] | 1.5 |
| | water | 54.5 |
| II | triethanol amine | 1.0 |
| | glycerin | 4.0 |
| III | stearic acid | 2.0 |
| | cetyl alcohol | 2.0 |
| | isopropyl myristate | 2.0 |
| | ATMUL® 124 [2] | 3.0 |
| | MARCOL® 130 [3] | 10.0 |
| | HS-100/UA | 20.0 |

[1] Magnesium aluminum silicate dispersant supplied by Vanderbilt Labs.
[2] Glyceryl stearate supplied by ICI
[3] Mineral oil supplied by Exxon This formulation is prepared by slowly adding VEEGUM® PRO under agitation at maximum shear to water at about 73° C. Then adding II with slow mixing until a smooth consistency is achieved at 70°-75° C. Finally, adding III and mixing while cooling. This greaseless antifungal cream serves a number of skin treating remedies.

| FOOT CREAM | | |
|---|---|---|
| D. | Ingredients | Wt. % |
| I | Deionized water | 54.0 |
| II | STARFOL® OO [1] | 6.0 |
| | STARFOL® wax CG [2] | 4.0 |
| | AROSURF® TA-100 [3] | 6.0 |
| | ADOL® 52 [4] | 6.0 |
| III | Pumice | 4.0 |
| | HS-100/UA | 20.0 |

[1] oleyl oleate
[2] cetyl ester mixture
[3] surfactant
[4] fatty alcohol, all supplied by Sherex Chemical Co.

This formulation is prepared by combining I and II at 70°–80° C. with rapid agitation, allowing the mixture to cool to 40° C. and then adding III while mixing and allowing the composition to cool to room temperature. The above formulation has a neutral pH and a viscosity of about 2800–3000 cps.

| AEROSOL FOOT POWDER | | |
|---|---|---|
| E. | Ingredients | Wt. % |
| | HS-100/UA | 10.0 |
| | Isopropyl myristate (IPM) | 13.4 |
| | Bentone® 38 [1] | 0.8 |
| | Ethanol | 0.8 |
| | Propellant-A46 [2] | 75.0 |

[1] Rheological additive
[2] 80% isobutane/20% propane

A dispersion of Bentone® in IPM is formed by high shear mixing for 15 minutes after which ethanol is added and mixing continued for 30 minutes more until a thick gel is formed. At low shear mixing HS-100/UA is gradually blended in small increments into the gel. After all of the HS-100/UA is added, mixing is continued for another 30 minutes. The resulting concentrate is then passed through a 60 mesh screen to remove large agglomerates and then homogenized at 6000 psi. The resulting concentrate is introduced into an epoxy-lined aerosol can, air is evacuated and propellant is charged.

| AEROSOL POWDER | | |
|---|---|---|
| F. | Ingredients | Wt. % |
| | HS-100/UA | 3.5 |
| | Dimethicone | 5.9 |
| | Bentone®-38 | 0.3 |
| | Ethanol | 0.3 |
| | Propellants | 90.0 |

This formulation is prepared by dispersing Bentone® in dimethicone at high-shear mixing for 15 minutes, after which ethanol is added and the mixing continued for an additional 30 minutes to form a thick gel. Then HS-100/UA is gradually blended in at low-shear mixing by additions in small increments. After all the HS-100/UA is added, low shear mixing is continued for an additional 30 minutes.

| DRY POWDER STICK | | |
|---|---|---|
| G. | Ingredients | Wt. % |
| | WITCAMIDE® 70 [1] | 28.0 |
| | WITCONOL® APM [2] | 25.0 |
| | White Mineral Oil | 5.0 |
| | Alpine talc, USP | 22.0 |

| DRY POWDER STICK | | |
|---|---|---|
| G. | Ingredients | Wt. % |
| | HS-100/UA | 20.0 |

(1) Stearamide in methyl ethyl ketone
(2) Myristyl ether of polypropylene glycol 3, both supplied by Witco chemical Co.

This formulation is prepared by heating the mixture of mineral oil and WITCONOL ® APM to 95° C. and then slowly adding WITCAMIDE ® 70 at the same temperature to produce a clear solution. To this is slowly added HS-100/UA and then talc in small amounts with continuous mixing until homogeneous. Perfume is optionally added and the resulting liquid is poured into a mold and allowed to cool.

In the above formulations A-G, the quaternized homopolymer complex shows excellent antifungal properties similar to undecylenic acid. Superior properties over the acid is realized by its ability to be dissolved in water and to significantly extend the duration of antifungal activity by forming a film on the skin. The present complex also acts as skin penetrant due to the film forming properties of the alkenyl lactam moieties in the polymer.

EXAMPLE 2

Preparation of Quaternized Polymer Complex

Undecylenic acid (18.5 g) was dissolved in methanol and reacted with 22 g of sodium methoxide (25% in methanol) to form the corresponding undecylenic acid sodium salt in 100 ml of methanol.

GAFQUAT ® 734* powder (100 g) derived from a 20% ethanolic solution of 500 g by alcohol evaporation under vacuum was then added to the sodium salt methanol solution at 60° C. and mixed at that temperature for a period of 2 hours. The sodium chloride formed was not removed and the solution was concentrated to a viscous consistency from which the GAFQUAT ® 734 undecylenate complex was recovered by precipitation with acetone to provide 121.5 g of powder as the quaternized complexed product containing about 5% units of vinyl pyrrolidone trimethylaminoethyl methacrylate chloride salt and 15% units of vinylpyrrolidone-trimethylaminoethylmethacrylate undecylenate salt units.

* poly(vinylpyrrolidone-trimethylaminoethylmethacrylate methyl chloride salt.

The above product can be substituted in any of the foregoing formulations to provide the described benefits.

In the above Examples 1 and 2, it will be understood that other salts of undecylenic acid, e.g. the potassium, zinc or calcium salt can be substituted for the sodium salt to provide the preferred antifungal products of this invention.

What is claimed is:

1. The antifungal quaternized block polymer consisting essentially of between about 75 and about 85 wt. % poly (vinyl lactam) units of the formula

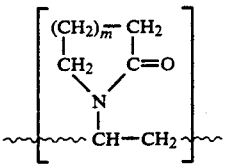

and between about 15 and about 25 wt. % of quaternized amino alkyl acrylamide lactam units defined as

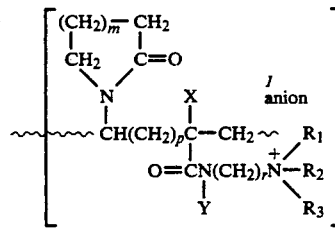

wherein said anion is between about 10 and about 90 wt. % halide and the balance of between about 90 and about 10 wt. % is $\overline{OCO(CH_2)_s CH}=CHZ$ and wherein m has a value of from 1 to 3; p has a value of from 1 to 5; r has a value of from 2 to 6; s has a value of from 4 to 14; each of X, Y and Z is independently hydrogen or $C_1$ to $C_4$ alkyl and each of $R_1$, $R_2$ and $R_3$ is independently $C_1$ to $C_4$ alkyl.

2. The polymer of claim 1 wherein m has a value of 1.

3. The polymer of claim 1 wherein x and y are each hydrogen.

4. The polymer of claim 3 wherein p has a value and r has a value of 2 or 3.

5. The polymer of claim 4 wherein $R_1$, $R_2$ and $R_3$ are each methyl.

6. The polymer of claim 1 wherein said anion is between about 25 and about 40 wt. % $Cl^-$ and between about 75 and about 60 wt. % $\overline{OCO(CH_2)_s CH}=CHZ$.

7. The polymer of claim 6 wherein s has a value of 9 and Z is hydrogen or methyl.

8. A water soluble antifungal composition comprising between about 3 and about 30 wt. % of the polymer of claim 1; between about 65 and about 90 wt. % of an inert carrier and between about 5 to about 10 wt. % of a surfactant.

9. The composition of claim 8 wherein said carrier is a dry particulate solid containing between about 0.5 and about 5 wt. % of a neutralizer.

10. The composition of claim 9 which additionally contains between about 1 and about 3 wt. % of an astringent.

11. The composition of claim 8 wherein said carrier is a cream base and the composition contains between about 1 and about 8 wt. % of a lubricant.

12. The composition of claim 11 which additionally contains between about 0.1 and about 5 wt. % moisturizer.

13. The composition of claim 8 wherein said carrier is an aqueous solution.

14. The composition of claim 8, wherein said carrier is an aerosol propellant and contains between about 0.1 and about 3 wt. % of a dehydrating agent.

15. The composition of claim 14 which is a foot powder or aerosol foot spray containing between about 0.1 and about 3 wt. % of a dehydrating agent.

16. The composition of claim 8 which is a dry deodorant stick which additionally contains between about and about 30 wt. % of a hardening agent.

17. The polymer of claim 6 wherein s has a value of 8 and Z is hydrogen.

* * * * *